(12) United States Patent
Desinger

(10) Patent No.: US 6,589,191 B2
(45) Date of Patent: Jul. 8, 2003

(54) MANUALLY ACTUABLE ULTRASONIC DISINTEGRATOR FOR BREAKING UP OR REMOVING HUMAN OR ANIMAL TISSUE

(76) Inventor: Kai Desinger, Rubensstrasse 108, D-12157 Berlin (DE)

( * ) Notice: Subject to any disclaimer, the term of this patent is extended or adjusted under 35 U.S.C. 154(b) by 0 days.

(21) Appl. No.: 09/848,025

(22) Filed: May 3, 2001

(65) Prior Publication Data

US 2002/0007200 A1 Jan. 17, 2002

(30) Foreign Application Priority Data

May 3, 2000 (DE) ......................... 100 21 529

(51) Int. Cl.[7] .................. A61H 1/00; A61H 1/02; A61H 5/00
(52) U.S. Cl. ........................................ 601/2
(58) Field of Search ............. 604/22; 606/128, 606/14; 433/119, 86

(56) References Cited

U.S. PATENT DOCUMENTS

| | | | |
|---|---|---|---|
| 4,804,364 A | * | 2/1989 | Dieras et al. ............... 604/22 |
| 4,931,047 A | | 6/1990 | Broadwin et al. |
| 5,012,797 A | | 5/1991 | Liang et al. |
| 5,116,343 A | * | 5/1992 | Ams et al. ............... 606/128 |
| 5,312,329 A | | 5/1994 | Beaty et al. |
| 5,626,560 A | * | 5/1997 | Soring ............... 604/22 |
| 5,702,360 A | * | 12/1997 | Dieras et al. ............... 604/22 |
| 5,776,092 A | | 7/1998 | Farin et al. |
| 6,139,320 A | * | 10/2000 | Hahn ............... 433/119 |

FOREIGN PATENT DOCUMENTS

| WO | PCT/US98/15709 | | 2/1999 | |
|---|---|---|---|---|
| WO | WO 00/54670 | * | 9/2000 | ........... A61B/17/22 |

* cited by examiner

*Primary Examiner*—Henry Bennett
*Assistant Examiner*—Sabrina Dagostino
(74) *Attorney, Agent, or Firm*—Beck & Tysver, P.L.L.C.

(57) ABSTRACT

There is provided a manually actuable ultrasonic disintegrator for the removal of human or animal tissue, which includes a sonotrode for the transmission of sound waves at its distal end to the tissue, an ultrasonic transducer which can be coupled to the sonotrode and a passage which extends lengthwise of the sonotrode for flushing and/or sucking away disintegrated or ablated tissue. In order to provide for the most effective possible application of ultrasonic waves into the tissue to be treated, the distal end of the sonotrode is in the form of a full surface outside which the flushing or suction removal passage extends.

27 Claims, 3 Drawing Sheets

MANUALLY ACTUABLE ULTRASONIC DISINTEGRATOR FOR BREAKING UP OR REMOVING HUMAN OR ANIMAL TISSUE

The invention concerns a manually actuable ultrasonic disintegrator for producing small passages in muscle tissue, in which both pressure amplitudes/shock waves are introduced into the surrounding tissue by way of power ultrasonics and also simultaneously a definedly thermal input can be applied to the surrounding tissue. The invention further serves for breaking up or removing human or animal tissue, comprising a sonotrode for the transmission or ultrasonic waves and locally delimited high-frequency voltage at its distal end to the tissue, an ultrasonic transducer which can be coupled to the proximal end of the sonotrode, and a passage which extends lengthwise of the sonotrode for flushing and/or sucking away disintegrated and/or cleared-away tissue and/or also for the transmission of sonotrode is also supplied, with its return electrode disposed in the direct proximity, with HF-voltage, by way of an external high-frequency voltage source. The sonotrode serves here for the simultaneously transmission of power ultrasonics and high-frequency voltage.

As is known, high-power ultrasonic waves are used for breaking up and/or clearing away tumour tissue. The tumour cells to be destroyed burst by virtue of the high pressure amplitudes and cavitation phenomena of the ultrasonic waves used, involving a high level of power density. A conventional ultrasonic disintegrator which can be actuated by hand includes an ultrasonic transducer, generally a piezo composite transducer, which is coupled directly or indirectly to a sonotrode. The sonotrode serves to transmit the ultrasonic waves produced by way of its active surface by the ultrasonic transducer, to the tissue to be cleared away, in the form of longitudinal waves. Preferably, in the known units, a mechanical amplitude transformer is connected between the ultrasonic transducer and the sonotrode, and the amplitude transformer provides that the ultrasonic waves which are transmitted to the sonotrode are of a suitable amplitude for disintegrating and clearing away or ablating the tumour cells. In the known units, the ultrasonic transducer, the amplitude transformer and the sonotrode are disposed in an elongate, handle-like housing, wherein the distal end of the sonotrode projects from a distal opening of the housing, at which the unit can be held and guided by hand.

Ultrasonic boring of materials is known from the industrial use of power ultrasonics. When suitable sonotrode geometries are involved, the high mechanical removal forces which power ultrasonics entail mean that holes or passages can be produced in the most widely varying materials, both hard and soft, without involving a substantial application of force.

At the present time predominantly pulsed laser systems are used, known by the term 'Trans-Myocardial Laser Revascularisation', in which respect in particular at the present time units from PLC/USA, CARDIO GENESIS/USA and United States Surgical Corporation/USA are used. With those pulsed laser systems, utilising the mechanism of what is referred to as photoablation, it is possible to form transmyocardial passages and, by virtue of the system involved, in that case thermally influenced edge zones are produced and also, due to the process of photoablation, shock waves. It will be noted however that the magnitude of the thermally influenced edge zone and the amplitudes and depth effect of the shock waves cannot be regulated and optimised separately from each other. In addition these systems are extremely expensive.

Surprisingly it was found that the successes achieved hitherto when using those high-energy laser systems can be essentially attributed to two laser-induced effects:

The production of intramuscular shock waves due to the process of photoablation of a fast local thermal explosion for vaporisation of the tissue in the target region and due to the thermal damage to the edge zones which is ultimately inevitable in principle with this kind of laser use (what is meant is the process of photoablation) and which, depending on the setting parameters which are respectively used for the above-indicated lasers, extends from carbonisation through coagulation to extreme hyperthermia. It was now possible to show in a manner that was entirely surprising even for experts in this field that the acute successes with this process, which have previously been reported, are essentially to be attributed to secondary effects of the shock waves produced and pressure amplitudes related thereto, and that the long-term successes are essentially to be attributed to the formation of the thermally influenced edge zone of the passages formed. In the case of the systems used in accordance with the state of the art, it is a priori completely impossible to optimise the mode of operation of the shock waves, that is to say the resulting pressure amplitude and pressure shock duration, as well as the depth action connected therewith, separately from the thermal edge damage effects which occur when implementing the process. It is likewise completely impossible for the clearly advantageous formation of a thermal edge zone to be further optimised separately from the shock waves to achieve and optimise the reported long-term successes.

In regard to the general disintegration of tissue it is not possible, in spite of the selectivity of ultrasound, to prevent relatively small vessels also being broken up. The consequence of this is haemorrhages which cannot be stemmed with the ultrasonic instrument as ultrasonic disintegration is an athermal process. In some known units that problem is resolved in that a hollow sonotrode which is preferably made from titanium is fed with a high frequency alternating current (HF-current). By virtue of suitable development of heat, the electromagnetic high-frequency fields generated at the distal end of the unit in the tissue coagulate the surrounding tissue, whereby finally a haemorrhage can be stemmed.

In that known generation of an electromagnetic high-frequency field, the sonotrode is connected as an electrode while the counterpart electrode is applied from the exterior to the human body—in the region of the treatment zone. That involves what is referred to as a monopolar arrangement in which the current flows through a large part of the body to the counterpart electrode which is generally disposed at one of the extremities.

U.S. Pat. No. 5,312,329 discloses a unit of the kind set forth in the opening part of this specification, in which there is provided a tubular hollow passage along the longitudinal axis of the sonotrode. The mouth opening of the passage is surrounded by the active surface of the sonotrode. The passage leads into the interior of the housing and is isolated from the other electronic and mechanical components in the housing. A vacuum pump can be connected to the passage so that tissue fragments or body fluid or the fumes produced upon coagulation, can be sucked away from the body by virtue of a vacuum produced in the cavity. The passage is likewise used to feed a fluid to the treatment area of the sonotrode in order to liquefy the cell fragments and thereupon suck them away. For that purpose the passage can be connected to a fluid container which provides the flushing fluid.

The consequence of the arrangement of sonotrode and passage, which is known from U.S. Pat. No. 5,312,329, is that the active surface of the sonotrode, that is to say the end face of the sonotrode at its distal end, which provides for the transmission of ultrasonic waves to the tissue, is relatively small, but the outside diameter is nonetheless relatively large due to the presence of the internal flushing passage. Because the removal rate of a sonotrode at constant frequency and constant amplitude is approximately proportional to the active surface thereof, the mouth opening of the passage in the active surface of the sonotrode causes a reduction in the active surface and thus the removal rate. That reduction is remedied by the outside diameter of the active annular surface being increased in size. In the case of that known unit however that means that the view of the tissue to be removed is limited, and in that way the area of use of the ultrasonic disintegrator is limited to structures of relatively large area. As however the main area of use of ultrasonic disintegrators in neurosurgery requires smaller and smaller miniaturised instruments in order to permit precise operation to be effected, that known instrument is not satisfactory. As the diameter of the sonotrodes of known units is some millimeters, for the reasons stated, the sonotrodes of those known units are also rigid and can no longer be used flexibly.

Therefore an object of the present invention is to provide a manually actuable ultrasonic disintegrator of the kind set forth in the opening part of this specification, which achieves a high ablation rate with an active sonotrode surface of small outside diameter, and which in that case also permits effective flushing and/or suction removal of cell fragments and also affords the possibility of thermally stemming haemorrhages by way of a local high-frequency current flow.

A further object of the invention is to provide a manually actuable ultrasonic disintegrator of the kind set forth in the opening part of this specification, which permits efficient ultrasonic boring of small passages in muscle tissue with at the same time application of thermal energy to the edge zones of the passage by means of a high-frequency electromagnetic alternating field, wherein the high-frequency current flow is implemented by way of a bipolar electrode arrangement in the proximity of the sonotrode.

The object of the present invention is achieved by a manually actuable ultrasonic disintegrator for the removal of human or animal tissue, which includes a sonotrode—preferably of varying length—for the transmission of ultrasonic waves at its distal end to the tissue, an ultrasonic transducer which can be coupled to the proximal end of the sonotrode and having an amplitude transformer, and a first passage which extends lengthwise of the sonotrode for flushing and/or suction removal of disintegrated and/or ablated tissue, and is characterised in that the distal end of the sonotrode has a full surface for transmission of the ultrasonic waves to the tissue, and that the passage extends outside the sonotrode. The term full surface is used here to denote a simply coherent or continuous surface, that is to say a surface whose outer contour or edge does not include any holes or recesses.

The advantages of the invention are in particular that the active surface of the sonotrode which influences the ablation rate is equal to the full surface, that is to say that the size of the active surface defined by its external contour is not reduced by hollow passages or bores. In addition the disintegrated tissue can be flushed out and/or sucked away through the first passage which extends outside the sonotrode, and the flushing and/or suction removal function is therefore implemented by the outwardly disposed first passage and possibly also by a second passage. In addition medicaments or other substances can be applied to the tissue or introduced into the tissue passage through that passage or passages of the sonotrode.

An advantageous embodiment of the present invention is achieved by the full surface at the distal end of the sonotrode coinciding with a flat distal end face of the sonotrode. The distal end face is the region which upon application of the ultrasonic disintegrator is applied to the treatment area and introduces the ultrasonic waves into the tissue which is to be ablated or bored.

In accordance with a further advantageous embodiment of the invention the sonotrode has a uniform full cross-section and is in the form of an elongate bar. The material preferably used for the sonotrode is titanium, but other body-compatible materials are also appropriate. A uniform cross-section of the sonotrode is advantageous as it is particularly simple to produce. By virtue of one or more outwardly disposed passages the diameter of the sonotrode can be selected to be particularly small, it is for example in the range of between 0.3 and 2 millimeters. By virtue of the small size of the sonotrode diameter it is also possible for the sonotrode to be of a flexible, bendable nature, whereby the possibility of attaining the desired treatment locations is improved and the system can also be used by way of flexible endoscopes or catheters.

In accordance with a further embodiment the sonotrode is arranged in a first tube whose internal cross-section is larger than the cross-section of the sonotrode so that the passage between the first tube and the sonotrode is of a predetermined passage cross-section. The foregoing arrangement of the sonotrode and the first passage permits a compact structure in respect of the distal end of the ultrasonic disintegrator. The passage mouth opening surrounds the sonotrode, whereby disintegrated tissue in the area around the sonotrode can be effectively sucked away.

In accordance with a further embodiment the sonotrode is arranged centrally in the first tube. This affords the advantage that the region around the distal end of the sonotrode is uniformly sucked away.

The sonotrode preferably projects coaxially from the distal mouth opening of the first passage. This is advantageous because the view on to the active surface of the sonotrode is made easier by virtue of the present arrangement, and the advantages of the invention, a maximum active surface with the smallest possible diameter for the sonotrode, are fully implemented. The reduced pressure in regard to the suction removal operation means nonetheless that the disintegrated tissue can be efficiently removed with the set-back suction removal tube.

In accordance with a further embodiment of the invention the sonotrode and the first tube are axially displaceable relative to each other in order to adjust the spacing between the ultrasonic wave-transmitting end face of the sonotrode and the mouth opening of the tube.

The ultrasonic transducer is preferably coupled to the sonotrode by way of an amplitude transformer. The amplitude transformer ensures that the ultrasonic waves transmitted to the sonotrode are of a sufficiently great amplitude which is suitable for disintegrating the cells to be removed. The ultrasonic amplitude can advantageously be suitably adapted to the respective conditions involved, by way of the alternating current generator which is connected from the exterior and which excites the ultrasonic transducer.

In accordance with a development of the invention, a proximal portion of the sonotrode, the amplitude transformer and the ultrasonic transducer are disposed in a bar-shaped housing from which a distal portion of the sonotrode projects, and the passage is passed through the housing. The common housing has connections for the electrical power supply, for the suction connections and/or flushing connections for the corresponding pumps. The housing is shaped to fit nicely to the hand so that the unit can be easily guided and used by hand.

In accordance with a further advantageous development of the invention in the region of the distal end the sonotrode has a first electrode surface and the tube surrounding the sonotrode has a second electrode surface. In this arrangement the sonotrode itself or the surrounding suction removal tube can be in the form of the sonotrode. The first and preferably also the second electrode surfaces can be connected to an external electrical HF-voltage source. The use of only one HF-electrode in the body of a patient and a counterpart electrode which is applied to the skin of the patient (using what is referred to as the monopolar treatment procedure) has the consequence that the current flowing in the body flows away in an area which is not accurately delimited and therefore results in uncontrolled and damaging influence on body-specific nerve cells. That is extremely dangerous precisely in relation to treatment in the region of the head of a patient. In accordance with the invention therefore in this embodiment, the first and second electrode surfaces form a bipolar electrode arrangement which provides that the field lines produced by way of the electrode surfaces preferably go from the first electrode surface to the second electrode surface. The present bipolar electrode arrangement therefore provides that, by virtue of the defined field line pattern, a locally precisely delimited area of tissue is coagulated in the area around the first and second electrode surfaces.

In accordance with a further advantageous embodiment of the invention the sonotrode and/or the passage tube comprises an electrical conductor which can be connected to the HF-voltage source. The surface of the sonotrode and/or the tube accordingly forms the first and/or second electrode surface. This embodiment permits an uncomplicated structure for the ultrasonic disintegrator as the HF-voltage source can be connected directly to the tube and the sonotrode. Furthermore there is no need to provide additional electrode surfaces.

Alternatively the sonotrode is formed from an electrically conducting material which is coated at least in a portion-wise manner with a dielectric insulating layer. In this embodiment, the first tube comprises a conducting material which on its inside surface can have a dielectric insulating layer which is necessary in particular when the sonotrode does not carry such an insulating layer.

In accordance with a further embodiment of the invention each sonotrode comprises an electrical insulator and the first electrode surface is a metal coating on the sonotrode. Similarly thereto, in a further embodiment, the tube is formed from an electrical insulator and the second electrode surface is a metal coating on the tube. It is advantageous in that respect that it is then possible, by virtue of the size and shape of the electrode surfaces, to make the coagulation region of a configuration corresponding to the area of use of the ultrasonic disintegrator.

In accordance with a particularly preferred embodiment of the invention, provided outside of the sonotrode is a second passage which also extends lengthwise of the sonotrode. The first passage and/or the second passage can be arranged at a predetermined location at the periphery of the sonotrode, they extend parallel to the sonotrode and then through the housing of the ultrasonic disintegrator and can be connected to external pumps (not shown) which operate one of the passages as a suction removal passage and the other as a flushing passage. The second passage can also be afforded by arranging concentrically on the first tube a second tube which forms the second passage with an annular cross-section, surrounding the first tube. The second tube preferably terminates a predetermined length in front of the distal end of the first tube.

In accordance with a further embodiment, to produce fine passages in muscle tissue for transmyocardial revascularisation (TMR) of the heart, the outer tube which here is of a somewhat spherically curved or flat configuration at the distal end can be applied to the muscle tissue. This part of the instrument which surrounds the sonotrode can both entirely enclose the sonotrode, being of a tubular configuration, but it can also be of a shell-shaped configuration relative to the longitudinal axis of the sonotrode, that is to say it can be open. By virtue of a defined advance movement of the inwardly disposed sonotrode by way of an actuating mechanism on the handle portion and activation both of the ultrasonic generator and also the HF-generator, fine passages can be bored in the muscle tissue by the sonotrode which is HF-supported by a local, high-frequency, electromagnetic alternating field. The ultrasound and the HF-field produce a pressure amplitude and also a thermal input in the passage which is being formed in the muscle tissue and thus initiate new formation of vessels.

Advantageous embodiments of the invention are described in greater detail hereinafter and illustrated in the drawing in which.

Figure 1:
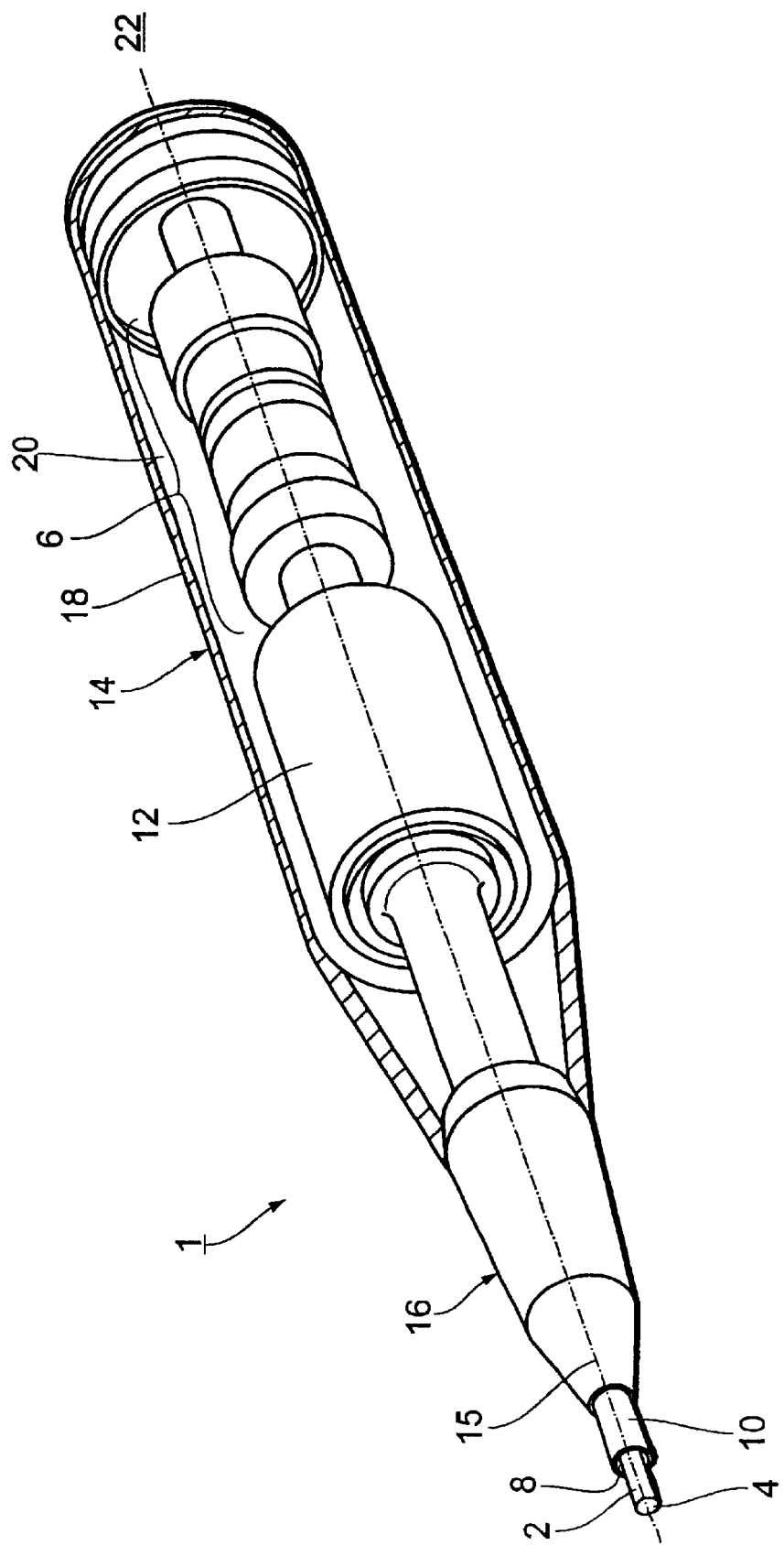
FIG. 1 shows an ultrasonic disintegrator in accordance with a first embodiment.

FIG. 1 shows a first embodiment of a manually actuable ultrasonic disintegrator. Shown therein is a substantially cylindrical housing 14 having a conical distal portion 16. The housing wall 18 is shown as being transparent so that the interior 20 of the housing 14 is visible. An ultrasonic transducer 6 and an amplitude transformer 12 are arranged at the longitudinal axis 15 of the housing 14. The distal region of the amplitude transformer 12 is connected to the sonotrode 2. The ultrasonic transducer 6 is disposed between the amplitude transformer 12 and the proximal end 22 of the housing 14. The ultrasonic transducer 6 is coupled to the amplitude transformer 12 and secured to the housing 14. An electrical alternating current generator (not shown) which can be connected to the unit from the exterior supplies the ultrasonic transducer 6 with the required electrical ac voltage and power in order so to excite the ultrasonic transducer 6 that it produces ultrasonic waves. Suction and flushing pumps (not shown) and possibly further electrical supply sources for additional functions can also be connected to the unit from the exterior.

The conical portion 16 of the housing 14 goes at its distal end into a tube 10 whose longitudinal axis coincides with the longitudinal axis 15 of the housing 14. A sonotrode 2 projects from the distal opening of the tube 10. The cylindrical sonotrode 2 is arranged centrally in the internal cross-section of the tube 10. The end face 4 of the sonotrode 2 has a circular peripheral contour; the sonotrode 2 is in the shape of a slender circular cylinder whose longitudinal axis aligns with the longitudinal axis 15 of the housing 14.

Alternatively the longitudinal axis of the sonotrode 2 can also include a predetermined angle, relative to the longitudinal axis 15 of the housing 14. At the distal end, the full cross-section of the circular cylinder forms the active surface of the sonotrode 2. The sonotrode 2 is preferably of a length which is a multiple of half the wavelength ($\lambda/2$) of the excited ultrasonic waves in order to permit a high level of ultrasonic power to be applied to the tissue. The sonotrode 2 is of a small cross-section and is preferably made from bendable material. The tube 10 which surrounds the sonotrode at a spacing with respect thereto and forms a passage 8 around the electrode is shortened at the distal end relative to the sonotrode 2 so that the distal tip of the unit at which tissue ablation is effected is formed only by the sonotrode.

The intermediate space between the sonotrode 2 and the tube 10 forms the distal region of a passage 8 which extends through the housing 4. The passage 8 is connected to a vacuum pump (not shown) for sucking away ablated or destroyed tissue. The passage 8 can be used both for sucking away tissue and also for flushing tissue in the treatment region. The passage 8 can in addition also be operated alternately for flushing and suction removal.

The sonotrode 2 comprises a solid material which is suitable for the transmission of ultrasonic waves. The annular hollow space between the sonotrode 2 and the tube 10 forms the mouth opening of the passage 8. The sonotrode 2 can be displaced along its longitudinal axis and then projects to a greater or lesser degree out of the mouth opening of the passage 8. Alternatively, the sonotrode is non-displaceable, and then the tube 10 is arranged to be displaceable in order to adapt the mouth opening of the passage to the needs of the respective treatment location involved. The sound waves to be applied are transmitted into the tissue to be treated, by way of the end face 4 of the sonotrode 2.

In the present embodiment, the sonotrode 2 forms a first electrode and the tube 10 forms a second electrode. The sonotrode 2 and the tube 10 are therefore made from a conductive material and are connected to an HF-voltage source (not shown). As the sonotrode 2 and the tube 10 are displaceable relative to each other, such an adjustment makes it possible to suitably adjust not only the mouth opening of the passage but also the form of the electromagnetic alternating field between the two electrodes and thus the corresponding coagulation area.

Figure 2:
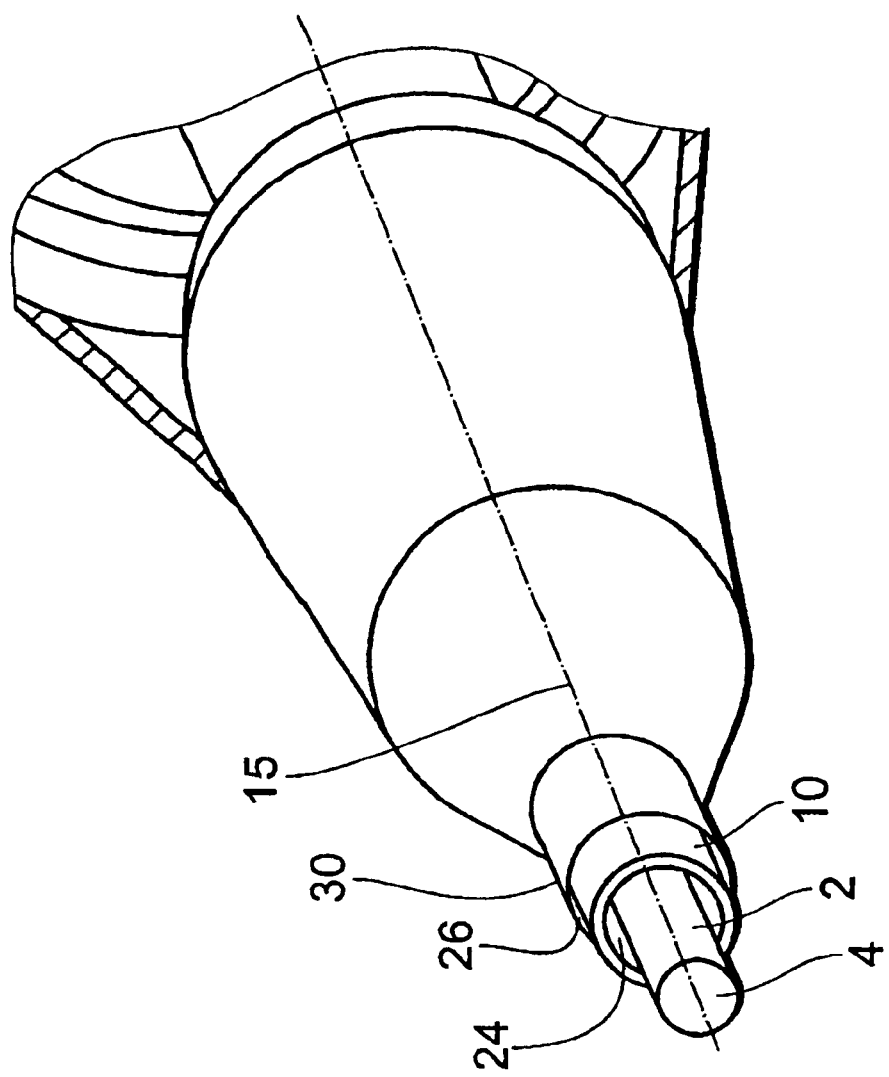
FIG. 2 is a view on an enlarged scale showing the sonotrode, the suction passage and the flushing passage of an ultrasonic disintegrator in accordance with a second embodiment.

FIG. 2 is a view on an enlarged scale showing a sonotrode 2 which is surrounded by two external passages, for example a suction passage 24 and a flushing passage 26. The cylindrical sonotrode 2 again projects out of the distal mouth opening of a tube 10. The longitudinal axis 3 of the cylindrical sonotrode 2 lies on the longitudinal axis of the tube 10 and the end face 4 of the sonotrode 2, which is in the form of a circular disc, forms the active surface of the sonotrode 2. The space between the sonotrode 2 and the tube 10 forms the mouth opening of a suction passage 24, that is to say that passage which is used for sucking away cell fragments. The suction passage 24 extends through the housing 14 to a proximal connecting portion to which suitable suction devices can be connected. A further tube 30 surrounds the tube 10 with the sonotrode 2 in such a way that a distal longitudinal portion of the tube 10 and of the sonotrode 2 project from the mouth opening of the tube 30.

The intermediate space between the tube 30 and the tube 10 forms the distal portion of a flushing passage 26, that is to say a passage which is used for feeding flushing fluid into the area around the sonotrode 2. The flushing passage 26 also extends through the housing 14.

Figure 3:
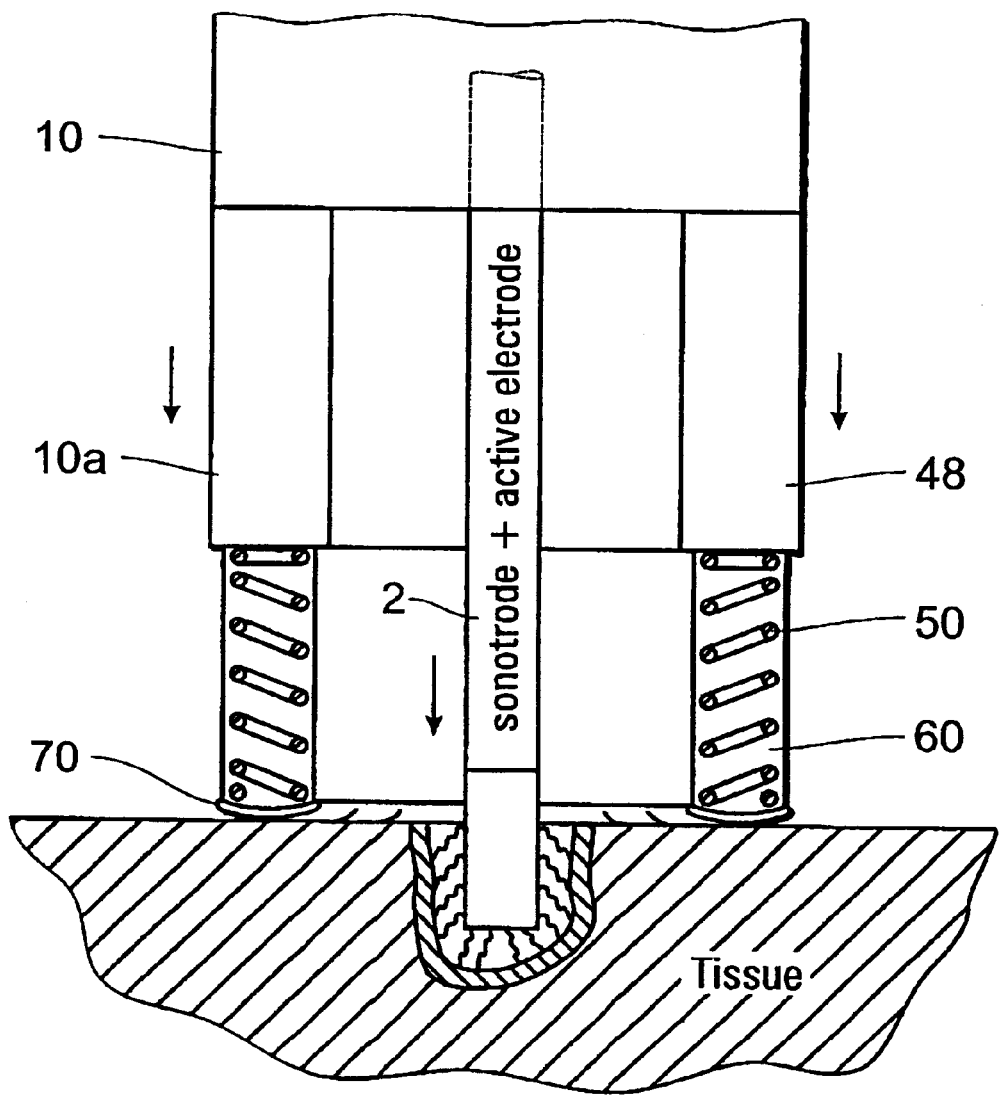
FIG. 3 is a view on an enlarged scale showing the distal end of the sonotrode in accordance with a third embodiment.

FIG. 3 shows a view on an enlarged scale of the sonotrode 2 of a further embodiment, only the distal end of the unit being illustrated. In this embodiment the sonotrode 2 is again arranged centrally in the tube 10. The wall of the tube 10 is broken away towards the distal end over a predetermined peripheral portion, for example 180°, and as a result is approximately of a semicircular cross-section. Provided at the axial edges of the remaining tube cross-section 10a are guides 48 in which are supported coil springs 50 which bear with their distal end against a displaceable distal wall portion 60. The distal wall portion 60 of the tube 10 is guided slidably in the axial guides 48 of the tube 10—against the biasing force of the compression springs 50—so that, in ultrasonic operation, the sonotrode 2 can penetrate into the adjoining tissue and in that case under the pressure of the user displaces the displaceable wall portion 60 of the tube 10 axially in the proximal direction.

By virtue of a defined advance movement of the inwardly disposed sonotrode 2, by way of an actuating mechanism, and with simultaneous activation of both the ultrasound and also the HF-generator, fine passages can be bored in the adjoining tissue by the sonotrode which is assisted by the electromagnetic alternating field. The application of energy by means of the sonotrode and/or a bipolar HF-energy application procedure also provide for thermal input into the passage wall, which can initiate the fresh formation of vessels.

In order to be able to operate the embodiment of the invention shown in FIG. 3 in a bipolar mode with an HF-ac voltage field, the sonotrode 2 is preferably connected to an external HF-generator, while the corresponding counterpart electrode 70 is formed at the end edge of the displaceable distal tube wall 60 and bears from the exterior against the tissue in which the sonotrode 2 is intended to produce a thin passage.

What is claimed is:

1. A manually actuable ultrasonic disintegrator for removing human or animal tissue, comprising
    a generally solid sonotrode having a distal end for the transmission of ultrasonic waves at the distal end into the tissue,
    an ultrasonic transducer adapted to be coupled to the sonotrode by way of an amplitude transformer, and
    a first tube having a first passage which extends lengthwise of the sonotrode, wherein the first passage is adapted for at least one of flushing and suction removal of at least one of disintegrated and ablated tissue,
    wherein the distal end of the sonotrode has a full surface for transmission of the ultrasonic waves to the tissue, and that the first passage extends outside the sonotrode.

2. The ultrasonic disintegrator as set forth in claim 1 wherein the sonotrode includes a distal end face, and the full surface at the distal end of the sonotrode coincides with the distal end face of the sonotrode.

3. The ultrasonic disintegrator as set forth in claim 1 characterised in that the sonotrode has a uniform full cross-section and is of a length which is substantially n×Lambda/2, wherein L is the wavelength of the ultrasonic waves produced and n is an integer equal to or greater than 1.

4. The ultrasonic disintegrator as set forth in claim 3 characterised in that the sonotrode is arranged centrally in the first tube.

5. An ultrasonic disintegrator as set forth in claim 4 characterised in that the first tube includes a distal end and the sonotrode projects from the distal end of the first tube axially by a predetermined lengthwise portion.

6. An ultrasonic disintegrator as set forth in claim 5 characterised in that the sonotrode and the first tube are axially displaceable relative to each other.

7. An ultrasonic disintegrator as set forth in claim 6 characterised by a second tube forming a second passage which extends outside and along the sonotrode.

8. An ultrasonic disintegrator as set forth in claim 7 characterised in that at least one of the first passage and the second passage is arranged at a predetermined location at the periphery of the sonotrode and extends parallel to the sonotrode.

9. An ultrasonic disintegrator as set forth in claim 7 characterised in that the second passage is arranged at a predetermined location at the outside periphery of the first tube and extends parallel to the sonotrode.

10. An ultrasonic disintegrator as set forth in claim 7 characterised in that the second tube is arranged concentrically around the first tube to form the second passage with an annular cross-section, which extends in the longitudinal direction of the sonotrode.

11. An ultrasonic disintegrator as set forth in claim 10, wherein the sonotrode includes a proximal end, and wherein the proximal end of the sonotrode, the amplitude transformer and the ultrasonic transducer are disposed in a housing, and that the passage is passed through the housing.

12. An ultrasonic disintegrator as set forth in claim 11 characterised in that in the region of the distal end the sonotrode has a first electrode surface, that one of the first and the second tube has a second electrode surface, and that at least one of the first and second electrode surfaces are adapted to be connected to an external electrical radio frequency voltage source.

13. An ultrasonic disintegrator as set forth in claim 12 characterised in that at least one of the sonotrode and the first or the second tube comprise an electrical conductor which are connectable to an external electrical radio frequency voltage source.

14. An ultrasonic disintegrator as set forth in claim 13 characterised in that the sonotrode comprises an electrical insulator and the first electrode surface is a metal coating on the sonotrode.

15. An ultrasonic disintegrator as set forth in claim 14 characterised in that at least one of the first and the second tube comprises an electrical insulator and the second electrode surface is a metal coating on one of the first and second tube.

16. An ultrasonic disintegrator as set forth in claim 15 characterised in that the sonotrode comprises an electrically conducting material and is at least partially coated with a dielectric insulating layer.

17. An ultrasonic disintegrator as set forth in claim 16 characterised in that at least one of the first tube and the second tube comprise an electrically conducting material and are provided at the inside surface with a dielectric insulating layer.

18. The ultrasonic disintegrator as set forth in claim 17 characterised in that the sonotrode and the first tube comprises an elastic material.

19. The ultrasonic disintegrator as set forth in claim 18 characterised in that the sonotrode and the first tube is adapted to be interchangeably secured to the untrasonic disintegrator.

20. The ultra sonic disintegrator as set forth in one of claims 1 wherein the first tube includes a distal end and characterised in that the first tube is partially broken away at the distal end of the first tube.

21. The ultrasonic disintegrator as set forth in claim 20 characterised in that a peripheral portion is broken away from the first tube at the distal end of the first tube.

22. The ultrasonic disintegrator as set forth in claim 21 characterised in that one of the first tube and the sonotrode are axially displaceable under a spring biasing force.

23. The ultrasonic disintegrator as set forth in claim 22 characterised in that the distal end of the first tube is displaceable axially under a spring biasing force relative to a proximally adjoining tube portion.

24. The ultrasonic disintegrator as set forth in claim 18 wherein the second tube comprises an elastic material.

25. The ultrasonic disintegrator as set forth in claim 19 wherein the second tube is adapted to be interchangeably secured to the ultrasonic disintegrator.

26. A manually actuable ultrasonic disintegrator for removing human or animal tissue, comprising a generally solid sonotrode, wherein the sonotrode has a uniform full cross-section and is of a length which is substantially n×Lambda/2, wherein L is the wavelength of the ultrasonic waves produced and n is an integer equal to or greater than 1, the sonotrode having a distal end for the transmission of ultrasonic waves at the distal end into the tissue, an ultrasonic transducer adapted to be coupled to the sonotrode by way of an amplitude transformer, and a first tube having a first passage which extends lengthwise of the sonotrode, wherein the sonotrode is arranged centrally in the first tube, wherein the first tube includes a distal end and the sonotrode projects from the distal end of the first tube axially by a predetermined lengthwise portion, wherein the first passage is adapted for at least one of flushing and suction removal of at least one of disintegrated and ablated tissue, wherein the distal end of the sonotrode has a full surface for transmission of the ultrasonic waves to the tissue, that the first passage extends outside the sonotrode, and that the sonotrode and the first tube are axially displaceable relative to each other.

27. A manually actuable ultrasonic disintegrator for removing human or animal tissue, comprising a generally solid sonotrode having a distal end for the transmission of ultrasonic waves at the distal end into the tissue, an ultrasonic transducer adapted to be coupled to the sonotrode by way of an amplitude transformer, and a first tube having a first passage which extends lengthwise of the sonotrode, the sonotrode having a distal end, wherein a peripheral portion of the distal end is partially broken away, wherein the first passage is adapted for at least one of flushing and suction removal of at least one of disintegrated and ablated tissue, wherein the distal end of the sonotrode has a full surface for transmission of the ultrasonic waves to the tissue, and that the first passage extends outside the sonotrode; and wherein the first tube or the sonotrode are axially displaceable under a spring biasing force.

* * * * *